United States Patent [19]
Kuno et al.

[11] Patent Number: 5,210,317
[45] Date of Patent: May 11, 1993

[54] METHOD OF PRODUCING ALDEHYDE BY OXIDATION OF PRIMARY ALCOHOL

[75] Inventors: Hideyuki Kuno; Makoto Shibagaki; Kyoko Takahashi; Hajime Matsushita, all of Yokohama, Japan

[73] Assignee: Japan Tobacco Inc., Tokyo, Japan

[21] Appl. No.: 768,769

[22] PCT Filed: Feb. 15, 1991

[86] PCT No.: PCT/JP91/00184
§ 371 Date: Oct. 17, 1991
§ 102(e) Date: Oct. 17, 1991

[87] PCT Pub. No.: WO91/12226
PCT Pub. Date: Aug. 22, 1991

[30] Foreign Application Priority Data

Feb. 19, 1990 [JP] Japan .................................. 2-36312

[51] Int. Cl.$^5$ ...................... C07C 47/00; C07C 45/27
[52] U.S. Cl. .................................. 568/420; 568/426; 568/449; 568/485
[58] Field of Search ............... 568/420, 426, 449, 485, 568/486, 487

[56] References Cited

U.S. PATENT DOCUMENTS

| | | | |
|---|---|---|---|
| 4,777,302 | 10/1988 | Haji et al. | 568/862 |
| 4,783,559 | 11/1988 | Matsushita et al. | 568/862 |
| 4,810,825 | 3/1989 | Matsushita et al. | 568/840 |
| 4,841,075 | 6/1989 | Matsushita et al. | 549/341 |
| 4,847,424 | 7/1989 | Matsushita et al. | 568/484 |
| 4,871,858 | 10/1989 | Matsushita et al. | 546/244 |
| 4,877,909 | 10/1989 | Mizusaki et al. | 568/880 |
| 4,880,937 | 11/1989 | Matsushita et al. | 546/344 |
| 4,910,177 | 3/1990 | Matsushita et al. | 502/65 |

OTHER PUBLICATIONS

Tetrahedron Letters, p. 3363 (1968).
Journal of the American Chemical Society, p. 85 (1963).
Organic Reactions, vol. 6, p. 207 (1951).
J. Organic Chem. vol. 51, pp. 240-242 (1951).

*Primary Examiner*—Werren B. Lone
*Attorney, Agent, or Firm*—Birch, Stewart, Kolasch & Birch

[57] ABSTRACT

Disclosed is a method of producing an aldehyde in which a primary alcohol is reacted with an oxidizing agent selected from the group consisting of ketone, aldehyde and quinone in the presence of a diluent which does not participate in the reaction, in the presence of a partially dehydrated zirconium hydroxide, so as to oxidize the primary alcohol into its corresponding aldehyde.

7 Claims, No Drawings

METHOD OF PRODUCING ALDEHYDE BY OXIDATION OF PRIMARY ALCOHOL

BACKGROUND OF THE INVENTION

1. Technical Field

The present invention relates to a method of manufacturing aldehyde by oxidizing a primary alcohol into the corresponding aldehyde, and more particularly, to an improvement in said method using a heterogeneous catalyst.

2. Background Art

In general, a serious difficulty is involved in the production of aldehyde by the oxidation reaction of primary alcohol. This difficulty is in good contrast to the ketone production by the oxidation of secondary alcohol, which can be achieved relatively easily by utilizing the Oppenauer oxidation.

Known methods of producing an aldehyde by the oxidation of a primary alcohol include, for example, the Collins oxidation disclosed in Tetrahedron Letters, p. 3363, 1968 and the DMSO-DCC method disclosed in Journal of the American Chemical Society, Vol. 85, 1963. However each of these known methods necessitates troublesome operations for purifying the product after the reaction. In addition, it is difficult to recover and re-use the reaction reagent, giving rise to serious air pollution or water contamination problems.

When it comes to the Oppenauer oxidation with a homogeneous catalyst system, a method of converting a primary alcohol into the corresponding aldehyde using aluminum isopropoxide as a catalyst in the presence of quinone acting as an oxidizing agent is known, as disclosed in Organic Reactions, Vol. 6, p. 207, 1951. However, it is difficult to re-use the catalyst in this method. Also, troublesome operations are required for the reaction and for the purifying step after the reaction.

In order to overcome the problems noted above, proposed in Published Unexamined Japanese Patent Application No. 1-151532 is a method of producing aldehyde at a high selectivity and a high yield, in which alcohol is reacted with a solid bromite in the presence of alumina or silica gel acting as a heterogeneous catalyst. However, this method is applicable only to benzyl alcohol and derivatives thereof, and thus, is not of sufficient practical value.

SUMMARY OF THE INVENTION

An object of the present invention is to provide a method of producing an aldehyde at a high selectivity and a high yield, in which a primary alcohol is oxidized in the presence of a heterogeneous catalyst which can be used again without difficulty.

To achieve this object, the present invention provides a method of producing an aldehyde, characterized in that a primary alcohol is reacted with an oxidizing agent selected from the group consisting of ketone, aldehyde and quinone in the presence of a partially dehydrated zirconium hydroxide, said reaction being carried out in a diluent which does not participate in the reaction, so as to oxidize the primary alcohol into the corresponding aldehyde.

DETAILED DESCRIPTION OF THE INVENTION

Specifically, what is most important in the present invention is that a partially dehydrated zirconium hydroxide is used as a heterogeneous catalyst. Naturally, it is important to describe first the partially dehydrated zirconium hydroxide used in the present invention.

If heated at about 500° C., zirconium hydroxide is completely dehydrated to form zirconia ($ZrO_2$). However, if heated at about 300° C. under atmospheric pressure, zircomium hydroxide is partially dehydrated to form a stable state. To be more specific, if the heat treatment is applied to zirconium hydroxide under the intermediate conditions noted above, about 17% of weight reduction takes place in the zirconium hydroxide within about 1 hour of the heat treatment. However, no substantial weight reduction takes place thereafter. The heat treatment for obtaining this particular state of the zirconium compound is not restricted to the above condition, and may be performed under a relatively wide range of conditions. For example, it is possible to apply heating at about 80° C. under a reduced pressure to obtain the same result. The partially dehydrated zirconium hydroxide thus obtained is in the form of a hard, white solid particle. Since the white solid particle is amorphous, it is impossible to apply X-ray diffractometry to the particle and, thus, the detailed chemical structure of the particle remains unclear. However, some conclusions may be drawn from the fact that the hydroxide is partially dehydrated. Specifically, it may be reasonable to conclude that the compound has a metal-oxygen-metal bond formed by the dehydration condensation and a remaining hydroxyl group directly attached to the metal. The partially dehydrated zirconium hydroxide, which is insoluble in organic solvents such as alcohol and in water, is a stable substance capable of performing the function of a heterogeneous catalyst. It has also been confirmed that the partially dehydrated zirconium hydroxide is low in its surface acidity and is capable of performing an ion-exchange function with various ions.

Zirconium hydroxide providing the raw material of the catalytic material used in the present invention can be obtained easily and at a low cost from zircon sand, paddeleyite, etc., which are present in large quantities as mineral resources on the earth. In preparing the partially dehydrated zirconium hydroxide, oxyzirconium chloride ($ZrOCl_2 \cdot 8H_2O$) is prepared first from the mineral resources noted above. Then an aqueous alkali solution is added to an aqueous solution of oxyzirconium chloride. As a result, the oxyzirconium chloride is decomposed so as to cause precipitation of fine gels of zirconium hydroxide. The solution is adjusted at a pH value of 6 to 7, and then, filtered so as to remove an excess aqueous solution of salts. As a result, the fine gels are agglomerated so as to form an elastic bulk gel. The bulk gel of zirconium hydroxide thus obtained is washed with a deionized water, cut into pieces of a suitable size and, then, dried so as to remove free water. Further, the heat treatment described previously is applied to the dried solid so as to obtain a partially dehydrated zirconium hydroxide.

The partially dehydrated zirconium hydroxide, which is pulverized into particles of a suitable size, can be used as it is as a catalyst. Alternatively, the pulverized particles may be supported on a suitable carrier such as alumina, activated carbon, silica gel, silica/alumina or zeolite.

The aldehyde forming reaction of the present invention is carried out in the presence of the partially dehydrated zirconium hydroxide described above. In the present invention, the reaction between a primary alcohol and an oxidizing agent such as ketone, aldehyde and/or quinone is carried out in a diluent which does not participate in the reaction, in the presence of the partially dehydrated zirconium hydroxide acting as a catalyst. The present inventors have found that the reaction proceeds as shown below so as to efficiently convert the primary alcohol into its corresponding aldehyde.

$$RCH_2OH \rightarrow RCHO$$

where R, which is not particularly restricted, may be a substituted or unsubstituted alkyl group, a substituted or unsubstituted cycloalkyl group or a substituted or unsubstituted aromatic group.

Either of a gaseous phase or liquid phase reaction can be employed in the present invention.

The ketone, aldehyde and/or quinone used in the present invention as an oxidizing agent is not particularly restricted. The preferred ketones used in the present invention include, for example, benzophenone, diisopropyl ketone, acetophenone, acetone, cyclohexanone and 2-cyclohexene-1-one. The preferable aldehydes used in the present invention include, for example, benzaldehyde, acetoaldehyde, acrolein and citral. Further, the preferred quinones used in the present invention include, for example p-benzoquinone, anthraquinone, α-naphthoquinone, and 2,3-dimethyl-1,4-naphthoquinone.

The diluent used in the present invention is not particularly restricted, as long as the diluent does not participate in the aldehyde forming reaction. For example, it is possible to use as the diluent inactive organic solvents, such as benzene, xylene, toluene, tetrahydrofuran, dioxane, diethylene glycol dimethyl ether, as well as a mixtures thereof. These organic solvents may also be used as a solvent for both the raw material and the oxidizing agent. When a gaseous phase reaction is used, inert gases such as a rare gas and a nitrogen gas may be used as the diluent. These inert gases may also be allowed to perform the function of a carrier gas. In a gaseous phase reaction, these inert gases may be used together with the inactive organic solvents noted above.

The diluent is very important in the present invention because the aldol condensation of the formed aldehyde becomes predominant in the absence of the diluent, leading to a marked decrease in the yield of the desired aldehyde, i.e., less than 1% of the aldehyde yield.

When a liquid phase reaction is used, the amount of the oxidizing agent may be 0.1 to 100%, preferably, 1.0 to 50.0%, based on the total amount of the raw material mixture, including the solvent. The reaction temperature may be 50° to 200° C., preferably, 80° to 150° C. The molar ratio of the raw material primary alcohol to the oxidizing agent can be selected appropriately from within a wide range of between 1/1 and 1/1000. After the reaction, solid materials are removed from the reaction mixture by means of filtration, followed by distilling the filtrate so as to obtain the desired aldehyde in a high purity.

The gaseous phase reaction can be effectively carried out by a flow-through system using a reaction tube loaded with the catalytic material specified in the present invention. Specifically, a raw material solution containing a primary alcohol, an oxidizing agent and, if desired, an inactive organic solvent, is evaporated and continuously supplied, together with a suitable carrier gas, into the reaction tube heated in advance to a predetermined temperature. The raw materials supplied to the reaction tube are brought into contact with the catalyst so as to carry out the desired reaction. The resultant reaction mixture flows out through the outlet port of the reaction tube. The outlet port of the reaction tube is cooled with ice so as to condense the reaction mixture flowing out of the reaction tube. It follows that a liquid reaction mixture is recovered. The reaction can be carried out at 20° to 300° C., preferably, at 60° to 250° C. Also, the molar ratio of the primary alcohol to the oxidizing agent can be selected appropriately from within a wide range of between 1/1 and 1/1000.

As described above, the method of the present invention allows the efficient conversion of a primary alcohol raw material into its corresponding aldehyde. It is important to note that the catalytic material used in the present invention is cheap and can be used again if washed with a suitable solvent, such as acetone. Also, a special production facility is not required. Additional advantages to be noted are that the reaction can be controlled easily, and that the formed product can be purified without difficulty.

Described in the following are an Example of producing the catalyst used in the method of the present invention and Examples of producing, aldehyde by the method of the present invention. Of course, the present invention is not restricted to these Examples.

EXAMPLE OF PRODUCING A CATALYST 200 g of oxyzirconium chloride (octahydrate) was dissolved in 10 liters of a deionized water. Then, a 1N aqueous solution of sodium hydroxide was gradually added to the resultant solution while stirring the solution so as to adjust the pH value of the solution at 6.80, thereby forming a hydrate gel. The hydrate gel was filtered so as to remove the salt aqueous solution, followed by washing the gel with fresh deionized water. The washing was repeated until chlorine ions ceased to be detected in the filtrate. Then, the gel was cut into small pieces with a knife, followed by spreading the cut pieces on a glass plate for drying at room temperature, so as to obtain 90 g of zirconium hydroxide. The resultant zirconium hydroxide was put in a deionized water, with the result that the pieces of the zirconium hydroxide were vigorously crushed to form grains of various sizes. The grains were separated by filtration, followed by drying of the separated grains in an enameled bucket at room temperature.

The granular zirconium hydroxide thus prepared was classified so as to collect grains passing through 24 to 60 meshes. The classified grains were subjected to a heat treatment at 300° C. for 5 hours within an electric furnace, so as to obtain a partially dehydrated zirconium hydroxide. The partially dehydrated zirconium hydroxide thus prepared was used as a catalyst in the Examples which follow.

EXAMPLE 1

Benzaldehyde was produced from benzyl alcohol as follows using the partially dehydrated zirconium hydroxide as a catalyst.

Specifically, 0.1 g of the catalyst, 10.8 mg (0.1 mmol) of benzyl alcohol and 10 mg of tridecane as an internal standard were added to 10 ml of xylene having 3.3 g of benzophenone dissolved therein, and a reaction was carried out for 2 hours under a reflux condition.

The reaction mixture was analyzed by means of gas chromatography and GC-MS. The reaction product was found to be benzaldehyde. Also, the product yield determined by the gas chromatography was 81.0%.

EXAMPLE 2

A reaction was carried out substantially as in Example 1, except that 12.2 mg (0.1 mmol) of 4-methylbenzyl alcohol was used in place of benzyl alcohol, and the reaction was carried out for 4 hours under reflux condition. After the reaction, the reaction product was identified and the product yield was measured as in Example 1. The reaction product was found to be 4-methyl benzaldehyde. The product yield was found to be 65.4%.

EXAMPLE 3

A reaction was carried out substantially as in Example 1, except that 13.0 mg (0.1 mmol) of 2-ethyl hexanol was used in place of benzyl alcohol, and the reaction was carried out for 4 hours under reflux condition. After the reaction, the reaction product was identified and the product yield was measured as in Example 1. The reaction product was found to be 2-ethylhexyl aldehyde. The product yield was found to be 50.9%.

EXAMPLE 4

A reaction was carried out substantially as in Example 1, except that 0.25 g of 1,4-benzoquinone was used in place of benzophenone used in Example 1, and the reaction was carried out for 4 hours under reflux condition. After the reaction, the reaction product was identified and the product yield was measured as in Example 1. The reaction product was found to be benzaldehyde. The product yield was found to be 85.8%.

EXAMPLE 5

A reaction was carried out substantially as in Example 1, except that 13.2 mg (0.1 mmol) of cinnamyl alcohol was used in place of benzyl alcohol and 0.25 g of the 1,4-benzoquinone was used in place of benzophenone used in Example 1. Further, the reaction was carried out for 16 hours under reflux condition in this experiment. After the reaction, the reaction product was identified and the product yield was measured as in Example 1. The reaction product was found to be 3-phenyl allyl aldehyde. The product yield was found to be 67.3%.

EXAMPLE 6

A reaction was carried out substantially as in Example 1, except that toluene was used in place of the xylene used in Example 1, and the reaction was carried out for 4 hours under reflux condition. After the reaction, the reaction product was identified and the product yield was measured as in Example 1. The reaction product was found to be benzaldehyde. The product yield was found to be 49.1%.

EXAMPLE 7

A reaction was carried out substantially as in Example 1, except that diethylene glycol dimethyl ether was used in place of the xylene used in Example 1, and the reaction was carried out for 4 hours under reflux condition. After the reaction, the reaction product was identified and the product yield was measured as in Example 1. The reaction product was found to be benzaldehyde. The product yield was found to be 30.1%.

EXAMPLE 8

A reaction was carried out substantially as in example 1, except that dioxane was used in place of the xylene used in Example 1, and the reaction was carried out for 4 hours under reflux condition. After the reaction, the reaction product was identified and the product was measured as in Example 1. The reaction product was found to be benzaldehyde. The product yield was found to be 34.1%.

EXAMPLE 9

Octyl aldehyde was produced from octyl alcohol as follows using the partially dehydrated zirconium hydroxide as a catalyst.

Specifically, 2.0 g of the catalyst was loaded in a reaction tube, i.e., a glass tube having an inner diameter of 4 mm, and uniformly fixed so as to form a catalyst bed. The reaction tube was set in an electric furnace. After the temperature within the furnace was elevated to 200° C., a reaction was carried out as follows.

In the first step, 50 ml of a xylene solution containing 65.0 mg (0.5 mmol) of octyl alcohol (starting material), 40 mg of tridecane (inner standard) and 16.5 g of benzophenone was prepared. The solution was supplied at a rate of 5 ml/hour into the reaction tube using a micro feeder. A nitrogen gas stream flowing at a rate of 1 ml/sec. was used as a carrier gas in the step of supplying the raw material solution into the reaction tube. The raw material solution passed through the catalyst bed together with the carrier gas, and the reaction mixture was withdrawn outside the furnace. In the withdrawing step, the reaction mixture was cooled with water or ice, so as to condense and liquefy the reaction mixture.

The liquid reaction mixture was analyzed by means of a gas chromatography and GC-MS. The reaction product was found to be octyl aldehyde. Also, the product yield determined by the gas chromatography was 74.3%.

EXAMPLE 10

A reaction was carried out substantially as in Example 9, except that 71.0 mg (0.5 mmol) of 3-cylohexylpropyl alcohol was used in place of the octyl alcohol used in Example 9. After the reaction, the reaction product was identified and product yield was measured as in Example 9. The reaction product was found to be 3-cyclohexylpropyl aldehyde. The product yield was found to be 69.0%.

EXAMPLE 11

A reaction was carried out substantially as in Example 1, except that 13.4 mg (0.1 mmol) of cinnamyl alcohol was used in place of benzyl alcohol and 3.3 g of benzaldehyde was used in place of the benzophenone used in Example 1. Further, the reaction was carried out for 4 hours under reflux condition in this experiment. After the reaction, the reaction product was identified and the product yield was measured as in Example 1. The main reaction product was found to be cinnamaldehyde. The product yield was found to be 56.2%.

REFERENCE EXAMPLE

Use of Acetone as Solvent

An aldehyde forming reaction was carried out as in Example 1, except that acetone was used in place of xylene used in Example 1.

The reaction mixture was analyzed with a gas chromatography and GC-MS. The reaction product was found to be benzaldehyde. Also, the product yield, which was determined by the gas chromatography, was found to be less than 1%.

What is claimed is:

1. A method for producing an aldehyde, comprising reacting a primary alcohol with an oxidizing agent selected from the group consisting of a ketone, an aldehyde, and a quinone, in the presence of a diluent which is inert to said reaction, and in the presence of a partially dehydrated zirconium hydroxide, so as to oxidize said primary alcohol to the corresponding aldehyde.

2. The method according to claim 1, wherein the oxidation of the primary alcohol into aldehyde is carried out as a liquid phase reaction.

3. The method according to claim 2, wherein said diluent is an inert organic solvent.

4. The method according to claim 3, wherein said inert organic solvent comprises at least one compound selected from the group consisting of benzene, xylene, toluene, tetrahydrofuran, dioxane, and diethylene glycol dimethyl ether.

5. The method according to claim 1, wherein the oxidation of the primary alcohol into aldehyde is carried out as a gaseous phase reaction.

6. The method according to claim 5, wherein said inert diluent is selected from the group consisting of a rare gas and nitrogen gas.

7. The method according to claim 6, wherein said rare gas or nitrogen gas is used as a carrier gas for the starting materials of said reaction.

* * * * *